(12) United States Patent
Iwanczyk et al.

(10) Patent No.: US 7,813,786 B2
(45) Date of Patent: *Oct. 12, 2010

(54) INTRAVASCULAR IMAGING DETECTOR

(75) Inventors: Jan S. Iwanczyk, Los Angeles, CA (US); Bradley E. Patt, Sherman Oaks, CA (US); Edward J. Hoffman, Los Angeles, CA (US)

(73) Assignee: Gamma Medica-Ideas, Inc., Northridge, CA (US)

( * ) Notice: Subject to any disclaimer, the term of this patent is extended or adjusted under 35 U.S.C. 154(b) by 342 days.

This patent is subject to a terminal disclaimer.

(21) Appl. No.: 11/400,146

(22) Filed: Apr. 7, 2006

(65) Prior Publication Data
US 2006/0195032 A1    Aug. 31, 2006

Related U.S. Application Data

(62) Division of application No. 09/754,103, filed on Jan. 3, 2001, now Pat. No. 7,328,058.

(60) Provisional application No. 60/174,440, filed on Jan. 4, 2000.

(51) Int. Cl.
*A61B 5/05* (2006.01)
*A61B 6/00* (2006.01)

(52) U.S. Cl. ........................ 600/425; 378/21
(58) Field of Classification Search ............... 600/425, 600/426, 427, 428, 429; 378/21, 22
See application file for complete search history.

(56) References Cited

U.S. PATENT DOCUMENTS

| | | | |
|---|---|---|---|
| 3,598,109 A | 8/1971 | Kobayashi et al. | |
| 3,670,719 A | 6/1972 | Kobayashi et al. | |
| 4,595,014 A | 6/1986 | Barrett et al. | |
| 4,628,203 A | 12/1986 | Reine et al. | |
| 4,647,445 A | 3/1987 | Lees | |
| 4,660,563 A | 4/1987 | Lees | |
| 4,877,599 A | 10/1989 | Lees | |
| 4,925,448 A | 5/1990 | Bazaral | |
| 4,937,067 A | 6/1990 | Lees | |
| 5,008,546 A * | 4/1991 | Mazziotta et al. | 250/366 |
| 5,024,791 A * | 6/1991 | Cusano et al. | 264/21 |
| 5,054,492 A | 10/1991 | Scribner et al. | |
| 5,076,278 A | 12/1991 | Vilkomerson et al. | |

(Continued)

FOREIGN PATENT DOCUMENTS

EP    0 788 766 A    8/1997

(Continued)

OTHER PUBLICATIONS

Chu et al., "An Evaluation of Cadmium Telluride Detectors for Computer Assisted Tomography," J. Computer Assisted Tomography, 1978, vol. 2, pp. 586-593.

(Continued)

*Primary Examiner*—Daniel Robinson
(74) *Attorney, Agent, or Firm*—Christie, Parker & Hale, LLP

(57) ABSTRACT

An apparatus for intravascular imaging to detect and characterize early stage, unstable coronary arty plaques. The detector works by identifying and localizing plaque-binding beta-emitting radiopharmaceuticals.

6 Claims, 16 Drawing Sheets

U.S. PATENT DOCUMENTS

| | | | |
|---|---|---|---|
| 5,088,492 | A | 2/1992 | Takayama et al. |
| 5,325,855 | A | 7/1994 | Daghighian et al. |
| 5,331,961 | A | 7/1994 | Inaba et al. |
| 5,424,546 | A | 6/1995 | Okada et al. |
| 5,429,133 | A | 7/1995 | Thurston et al. |
| 5,449,921 | A * | 9/1995 | Baba .......................... 250/583 |
| 5,465,119 | A | 11/1995 | Demos |
| 5,493,595 | A | 2/1996 | Schoolman |
| 5,510,466 | A | 4/1996 | Krieger et al. |
| 5,651,047 | A | 7/1997 | Moorman et al. |
| 5,672,153 | A | 9/1997 | Lax et al. |
| 5,707,354 | A | 1/1998 | Salmon et al. |
| 5,711,931 | A | 1/1998 | Dean et al. |
| 5,716,595 | A | 2/1998 | Goldenberg |
| 5,726,153 | A | 3/1998 | Lees et al. |
| 5,743,261 | A | 4/1998 | Mainiero et al. |
| 5,751,781 | A | 5/1998 | Brown et al. |
| 5,803,914 | A | 9/1998 | Ryals et al. |
| 5,811,814 | A | 9/1998 | Leone et al. |
| 5,815,057 | A | 9/1998 | Hoffman et al. |
| 5,836,882 | A | 11/1998 | Frazin |
| 5,871,449 | A | 2/1999 | Brown |
| 5,906,636 | A | 5/1999 | Casscells, III et al. |
| 5,923,038 | A | 7/1999 | DiFilippo et al. |
| 5,924,997 | A | 7/1999 | Campbell |
| 5,935,075 | A | 8/1999 | Casscells et al. |
| 5,961,457 | A | 10/1999 | Raylman et al. |
| 6,031,892 | A | 2/2000 | Karellas |
| 6,031,893 | A | 2/2000 | Karella |
| 6,038,468 | A | 3/2000 | Rex |
| 6,041,132 | A | 3/2000 | Isaacs et al. |
| 6,113,593 | A | 9/2000 | Tu et al. |
| 6,114,703 | A | 9/2000 | Levin et al. |
| 6,167,297 | A | 12/2000 | Benaron |
| 6,295,680 | B1 | 10/2001 | Wahl et al. |
| 6,331,703 | B1 * | 12/2001 | Yarnall et al. ............. 250/336.1 |
| 6,456,869 | B1 * | 9/2002 | Raylman et al. ............ 600/436 |
| 6,459,919 | B1 | 10/2002 | Lys et al. |
| 6,510,336 | B1 * | 1/2003 | Daghighian et al. ......... 600/427 |
| 6,521,894 | B1 | 2/2003 | Iwanczyk et al. |
| 6,534,770 | B2 * | 3/2003 | Miller et al. ........... 250/363.02 |
| 6,553,248 | B1 | 4/2003 | Gagnon et al. |
| 6,561,047 | B1 | 5/2003 | Gladney et al. |
| 6,643,538 | B1 | 11/2003 | Majewski et al. |
| 6,661,865 | B1 | 12/2003 | Popilock |
| 6,671,541 | B2 | 12/2003 | Bishop et al. |
| 6,690,966 | B1 * | 2/2004 | Rava et al. ................... 600/473 |
| 6,782,289 | B1 * | 8/2004 | Strauss ........................ 600/436 |
| 6,801,648 | B2 | 10/2004 | Cheng |
| 6,920,346 | B2 | 7/2005 | Kazandjian et al. |
| 7,328,058 | B2 * | 2/2008 | Iwanczyk et al. ........... 600/425 |
| 2002/0022799 | A1 | 2/2002 | Apple |
| 2002/0168317 | A1 | 11/2002 | Daighighian et al. |

FOREIGN PATENT DOCUMENTS

| | | |
|---|---|---|
| WO | WO 89/10760 | 11/1989 |
| WO | WO 00/27278 | 5/2000 |
| WO | WO 01/64277 | 9/2001 |

OTHER PUBLICATIONS

Demos, Sasha M., et al., "In Vitro Targeting of Antibody-Conjugated Echogenic Liposomes for Site-Specific Ultrasonic Image Enhancement," J. Pharm. Sci., Feb. 1997, vol. 86, No. 2, pp. 691-695.

Kaufman et al., "An Evaluation of Semiconductors for Positron Cameras," JCAT, 1978, vol. 2, No. 5, pp. 651.

Kaufman et al., "An Evaluation of Semiconductor Detectors for Positron Tomography," IEEE Trans. Nucl. Sci., 1979, NS-26(1), pp. 648-653.

Kaufman et al., "Ghost Imaging in MRI," Studies in Health Technology and Informatics, 2001, vol. 81, pp. 229-235.

Narula, Jagat, M.D., Ph.D., et al., "Noninvasive Localization of Experimental Atherosclerotic Lesions With Mouse/Human Chimeric 2D3 F (ab')$_2$ Specific for the Proliferating Smooth Muscle Cells of Human Atheroma," Circulation, Aug. 1, 1995, vol. 92, No. 3, pp. 474-484.

Ohdaira, Takeshi, MD, et al., "Inoperative Localization of Colorectal Tumors in the Early Stages Using a Marking Chip Detector System," Dis. Colon Rectum, Oct. 1999, vol. 42, No. 10, pp. 1353-1355.

Ortendahl et al., "Recovery of Loss of Spatial Resolution at Depth in Planar Images," Nuclear Instruments and Methods, 1982, vol. 193, pp. 163-167.

Parsons, Richard E., MD, "Fluoroscopically Assisted Thromboembolectomy: An improved Method for Treating Acute Arterial Occlusions," Ann. Vasc. Surgery, 1996, vol. 10, No. 3, pp. 201-210.

Schlosser et al., "A Practical Gamma-Ray Camera System Using High-Purity Germanium," IEEE Transaction on Nuclear Science, 1974, vol. 21, No. 1, pp. 658-664.

Lees, Ann M., et al. "Imaging Human Atherosclerosis with $^{99m}$Tc-labeled Low Density Lipoproteins," Arteriosclerosis, Sep./Oct. 1988, vol. 8, pp. 461-470.

Elmaleh, David R., et al., "Rapid Noninvasive Detection of Experimental Atherosclerotic Lesions with Novel $^{99m}$Tc-labeled Diadenosine Tetraphosphates," Proc. Natl. Acad. Sci., Jan. 1988, vol. 95, pp. 691-695, USA.

Vallabhajosula, S., and Fuster, V., "Atherosclerosis: Imaging Techniques and the Evolving Role of Nuclear Medicine," J Nuc. Med., Nov. 1997, vol. 38, No. 11, pp. 1788-1796.

Supplementary European Search Report for European Application No. 01902972.7, dated Sep. 13, 2004.

The Patent Office-An Executive Agency of the Department of Trade and Industry, "The Patents & Design Journal", United Kingdom, No. 6099, Apr. 12, 2006 (2 pgs.).

* cited by examiner

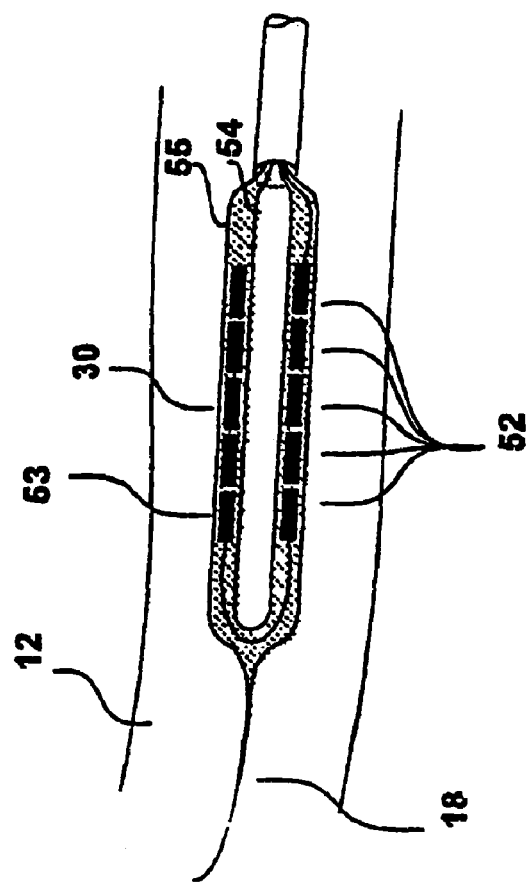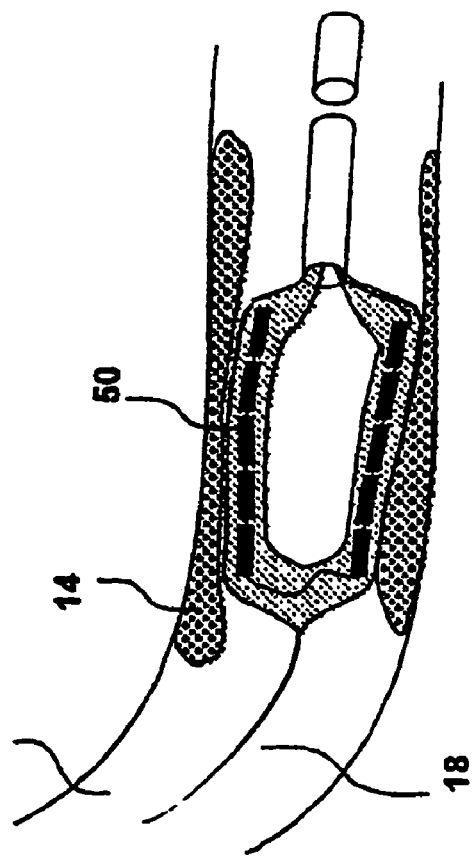
FIG. 11
FIG. 12

INTRAVASCULAR IMAGING DETECTOR

CROSS-REFERENCE TO RELATED APPLICATION(S)

The present application is a divisional of U.S. patent application Ser. No. 09/754,103, filed Jan. 3, 2001 now U.S. Pat. No. 7,328,058, which claims benefit under 37 C.F.R. §1.78 of U.S. Provisional Application No. 60/174,440, filed Jan. 4, 2000, and entitled "Intravascular Imaging Detector," the entire contents of both of which are incorporated by reference herein. The present application also incorporates U.S. Pat. No. 6,782,289, issued on Aug. 24, 2004, by reference herein.

BACKGROUND OF THE INVENTION

Coronary angiography is used to identify and measure the luminal dimensions of blood vessels. Angiography however, cannot provide information about plaque content.

The subject invention addresses this deficiency by placing an imaging detector into the arteries to detect and characterize early-stage, unstable coronary artery plaques. This can provide a signature relevant to the 70% of heart attacks that are caused by minimally obstructive, unstable plaques that are too small to be detected by angiography.

The present invention describes construction of an intravascular imaging detector which works in concert with systemically administered plaque-binding beta-emitting radiopharmaceuticals such as 18-Fluorodeoxyglucose (18-FDG). The apparatus of the present invention accomplishes these benefits by identifying and localizing these plaque-binding beta or conversion electron emitting radiopharmaceuticals.

Intravascular imaging probes constructed in accordance with the principles of the present invention yield detectors, which satisfy the difficult constraints of the application in terms of size of the device, needed sensitivity, and conformance to the intravascular requirements.

The apparatus of the present invention will allow new targeted and cost effective therapies to prevent acute coronary artery diseases such as: unstable angina, acute myocardial infarction, and sudden cardiac death.

The present invention generally provides an apparatus for intravascular imaging to detect and characterize early-stage, vulnerable coronary artery plaques. The detector works by identifying and localizing plaque-binding beta-emitting radiopharmaceuticals.

The apparatus of the present invention includes a radiation detector(s) with a predetermined intrinsic spatial resolution, typically between 1-8 mm, and preferably between 1-3 mm. In some embodiments, the detector is in the form of a detector array. The detector array can include a plurality of detector units or pixels built onto a single chip or separate chips. The detector(s) are typically integrated into an intravascular catheter so that it can be manipulated through the body lumen, optionally using a guidewire in much the same way as a balloon catheter for angioplasty.

Optionally, the detectors of the present invention can be embedded within a balloon or other expansible structure such as a flexible membrane, which is collapsed or deflated during guidance through the body lumen. The structure can then be deployed at a target site so that the detector is pressed up against the inside of the artery wall bringing the detector in contact with the plaque. This optimizes the particle to gamma and signal to background ratios for charged particle imaging.

During transit through the artery, software or other analyzing means may decode the data obtained by the detector to operate in a search mode. The search mode is typically performed by summing all of the pixels of the detectors to obtain a fast gross count. Once a threshold gross count is detected (e.g. a high count rate region is localized), the software can switch to an imaging mode to produce a higher resolution image to provide more detail of the plaque. For embodiments using a balloon, the balloon can be kept in a deflated configuration during the fast gross count and the balloon can be inflated when the detectors are switched to the imaging mode.

Exemplary radiation detectors include: 1) Scintillators; 2) Imaging plates; 3) Semiconductors; and 4) Ionization chambers. Each of the described embodiments yields a detector which satisfies the difficult constraints of the application in terms of size of the device, needed sensitivity, and conformance to the intravascular requirements.

The apparatus of the present invention preferably provides both high beta particle detection efficiency and sufficient sensitivity in the very small detector volume afforded by an intravascular or other medical catheter tip.

Monte Carlo simulations developed for tracking beta trajectories and deposited energy have been used to guide the choice of material and shape and size of the pixel elements. Whereas the volume of the detector is limited by the arterial lumen, the correct pixel dimensions (laterally) are comparable with the beta range (in the specific detector). Monte Carlo simulations have been performed for F-18 positrons and T1-204. The simulations have been used as a basis for the detector design.

The sensitivity has also been directly measured for beta particles for each of the fabricated prototype detectors. This has been done with T1-204 and F-18 beta emitters.

The apparatus of the present invention allows for high efficiency for betas and very low detection efficiency for 511 keV gammas. Generally we have precluded materials that have either high atomic number or high density Gasses, liquids, light plastics and thin low-Z semiconductors have been found to be preferable in this respect to high Z compound semiconductors.

The sensitivity and immunity to gamma background is confirmed with the use of filter paper disks containing known F-18 source activity. A series of measurements is taken from which mean and standard deviation counts per second is calculated. A second series of the measurements is taken in the same configuration with exception that a 0.2 mm thick piece of stainless steel is placed in front of detector face this time. By dividing the results from the first set of measurements by the amount of the activity on the disk, the combined (beta and photon) sensitivity is calculated. The beta sensitivity is calculated by subtracting the pure photon rate from the combined count rate. The results are analyzed versus energy thresholds ranging from the noise level up to 495 keV (Compton edge for 511 keV).

The apparatus of the present invention allows the device to be operated in such a way as to allow the detector to be pressed up against the inside of the artery wall. Three of the described embodiments: the gas scintillator, the semiconductor detector and the ionization chamber detector are designed to be embedded within a balloon or other expansible structure which although deflated during guidance through the artery or other body lumen, can be inflated when at a plaque site. The balloon can be alternatively deflated during transit through the artery and then inflated when at a suspicious suite. In addition the detector has the ability to operate in a search mode by summing all of the pixel responses to obtain a fast gross count during transit through the artery. The apparatus is switched to an "imaging" mode to obtain high-resolution detail of the plaque when a high-count rate region is localized.

The apparatus of the present invention allows for spatial resolution on the order of 1 mm, which is sufficient to interrogate a plaque. This also is of the same order as the beta range. The spatial resolution is confirmed by measurement of the point spread function and the inter-element cross talk of the imager to beta particles.

The apparatus of the present invention allows construction to maximize its passive properties, which are attractive due to the higher degree of safety during procedures. The preference had been given to detectors composed of inert materials due to the higher degree of safety during procedures.

The detection mechanisms of the apparatus of the present invention allow for the highest signal and sensitivity of the detector. This criterion favors the semiconductor detector approach, which offers the most efficient energy transfer.

The apparatus of the present invention allows for a construction that can be integrated with the catheter and guidewire.

SUMMARY OF THE INVENTION

The present invention generally provides an apparatus for intravascular imaging to detect and characterize early-stage, vulnerable coronary artery plaques. The detector works by identifying and localizing plaque-binding beta-emitting radiopharmaceuticals.

The apparatus of the present invention includes a radiation detector(s) with a predetermined intrinsic spatial resolution, typically between 1-8 mm, and preferably between 1-3 mm. In some embodiments, the detector is in the form of a detector array. The detector array can include a plurality of detector units or pixels built onto a single chip or separate chips. The detector(s) are typically integrated into an intravascular catheter so that it can be manipulated through the body lumen, optionally using a guidewire in much the same way as a balloon catheter for angioplasty.

Optionally, the detectors of the present invention can be embedded within a balloon or other expansible structure such as a flexible membrane, which is collapsed or deflated during guidance through the body lumen. The structure can then be deployed at a target site so that the detector is pressed up against the inside of the artery wall bringing the detector in contact with the plaque. This optimizes the particle to gamma and signal to background ratios for charged particle imaging.

During transit through the artery, software or other analyzing means may decode the data obtained by the detector to operate in a search mode. The search mode is typically performed by summing all of the pixels of the detectors to obtain a fast gross count. Once a threshold gross count is detected (e.g. a high count rate region is localized), the software can switch to an imaging mode to produce a higher resolution image to provide more detail of the plaque. For embodiments using a balloon, the balloon can be kept in a deflated configuration during the fast gross count and the balloon can be inflated when the detectors are switched to the imaging mode.

Exemplary radiation detectors include: 1) Scintillators; 2) Imaging plates; 3) Semiconductors; and 4) Ionization chambers. Each of the described embodiments yields a detector which satisfies the difficult constraints of the application in terms of size of the device, needed sensitivity, and conformance to the intravascular requirements.

The apparatus of the present invention preferably provides both high beta particle detection efficiency and sufficient sensitivity in the very small detector volume afforded by an intravascular or other medical catheter tip.

Monte Carlo simulations developed for tracking beta trajectories and deposited energy have been used to guide the choice of material and shape and size of the pixel elements. Whereas the volume of the detector is limited by the arterial lumen, the correct pixel dimensions (laterally) are comparable with the beta range (in the specific detector). Monte Carlo simulations have been performed for F-18 positrons and Tl-204. The simulations have been used as a basis for the detector design.

The sensitivity has also been directly measured for beta particles for each of the fabricated prototype detectors. This has been done with Tl-204 and F-18 beta emitters.

The apparatus of the present invention allows for high efficiency for betas and very low detection efficiency for 511 keV gammas. Generally we have precluded materials that have either high atomic number or high density. Gasses, liquids, light plastics and thin low-Z semiconductors have been found to be preferable in this respect to high Z compound semiconductors.

The sensitivity and immunity to gamma background is confirmed with the use of filter paper disks containing known F-18 source activity. A series of measurements is taken from which mean and standard deviation counts per second is calculated. A second series of the measurements is taken in the same configuration with exception that a 0.2 mm thick piece of stainless steel is placed in front of detector face this time. By dividing the results from the first set of measurements by the amount of the activity on the disk, the combined (beta and photon) sensitivity is calculated. The beta sensitivity is calculated by subtracting the pure photon rate from the combined count rate. The results are analyzed versus energy thresholds ranging from the noise level up to 495 keV (Compton edge for 511 keV).

The apparatus of the present invention allows the device to be operated in such a way as to allow the detector to be pressed up against the inside of the artery wall. Three of the described embodiments: the gas scintillator, the semiconductor detector and the ionization chamber detector are designed to be embedded within a balloon or other expansible structure which although deflated during guidance through the artery or other body lumen, can be inflated when at a plaque site. The balloon can be alternatively deflated during transit through the artery and then inflated when at a suspicious suite. In addition the detector has the ability to operate in a search mode by summing all of the pixel responses to obtain a fast gross count during transit through the artery. The apparatus is switched to an "imaging" mode to obtain high-resolution detail of the plaque when a high-count rate region is localized.

The apparatus of the present invention allows for spatial resolution on the order of 1 mm, which is sufficient to interrogate a plaque. This also is of the same order as the beta range. The spatial resolution is confirmed by measurement of the point spread function and the inter-element cross talk of the imager to beta particles.

The apparatus of the present invention allows construction to maximize its passive properties, which are attractive due to the higher degree of safety during procedures. The preference had been given to detectors composed of inert materials due to the higher degree of safety during procedures.

The detection mechanisms of the apparatus of the present invention allow for the highest signal and sensitivity of the detector. This criterion favors the semiconductor detector approach, which offers the most efficient energy transfer.

The apparatus of the present invention allows for a construction that can be integrated with the catheter and guidewire.

BRIEF DESCRIPTION OF THE DRAWINGS

The above and other features of the present invention may be more fully understood form the following detailed description, taken together with the accompanying drawings, wherein similar reference characters refer to similar elements throughout and in which:

FIG. 11 is a fragmentary, exploded perspective view illustrating, in simplified form one embodiment of an apparatus constructed in accordance with the present invention, employing strips of semiconductor particle detectors. In this figure the balloon is deflated during guidance through the artery towards a plaque.

FIG. 12 is a fragmentary, exploded perspective view illustrating, in simplified form one embodiment of an apparatus constructed in accordance with the present invention, employing strips of semiconductor particle detectors. In this figure the balloon is inflated in the artery at the site of plaque.

DESCRIPTION OF THE SPECIFIC EMBODIMENTS

Figure 1:
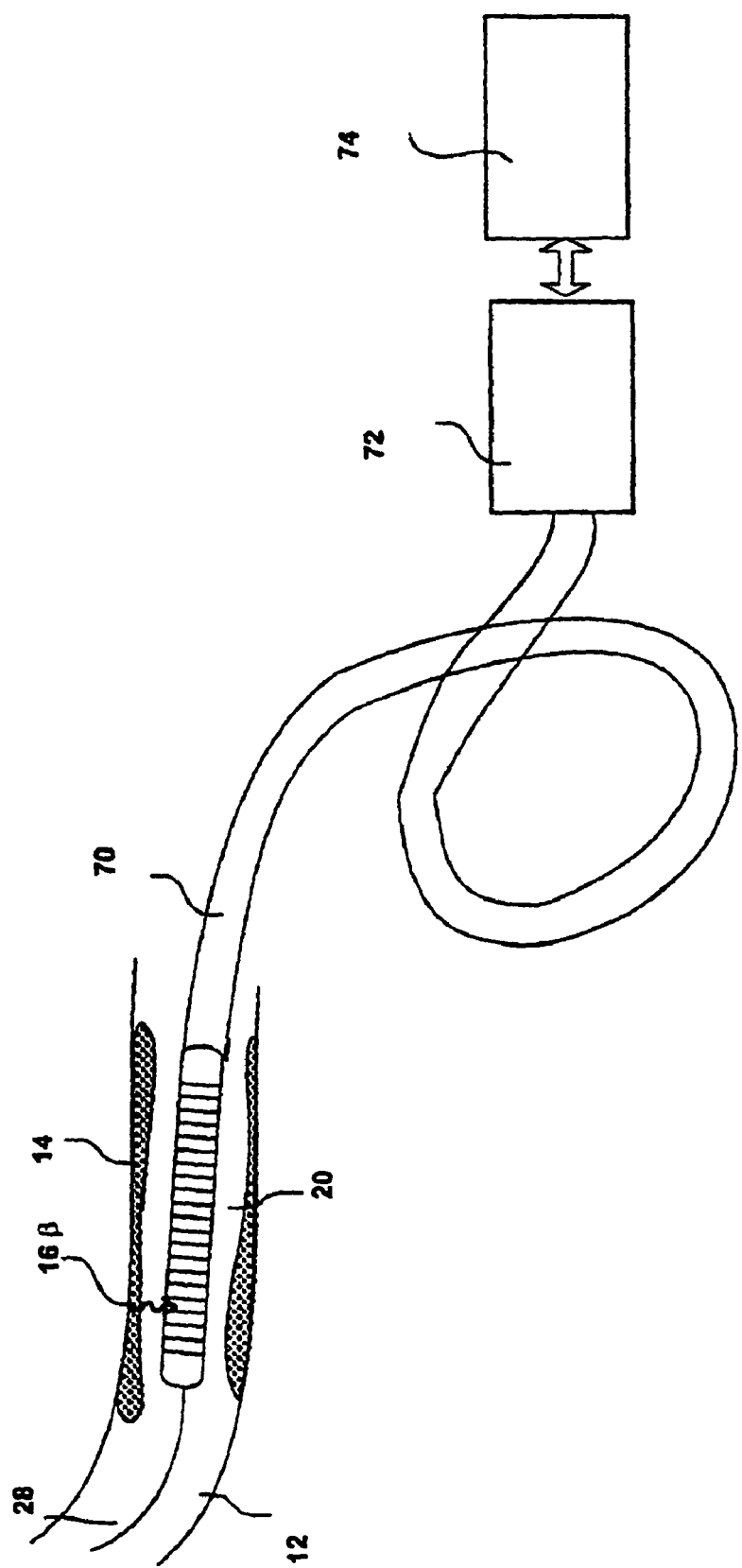
FIG. 1 is a schematic view of an apparatus constructed in accordance with the present invention for intravascular imaging to detect and characterize early-stage, unstable coronary artery plaques.

Referring to FIG. 1 an apparatus for imaging in arteries 12 to detect and characterize early-stage, unstable coronary artery plaques 14 is comprised of an imaging probe tip 20 which includes a miniature beta sensitive detector. It works by identifying and localizing plaque-binding radiopharmaceuticals that emit beta particles 16. The radiation detector has an intrinsic spatial resolution of approximately 1-3 mm. It is integrated into an arterial catheter 70 so that it can be manipulated through the artery by a guidewire 28 in much the same way as a balloon catheter for angioplasty. The detector of the present invention once integrated into the catheter 70 connects to data acquisition electronics 72 and a computer and display 74, which provides an image of the distribution of plaque.

Figure 2:
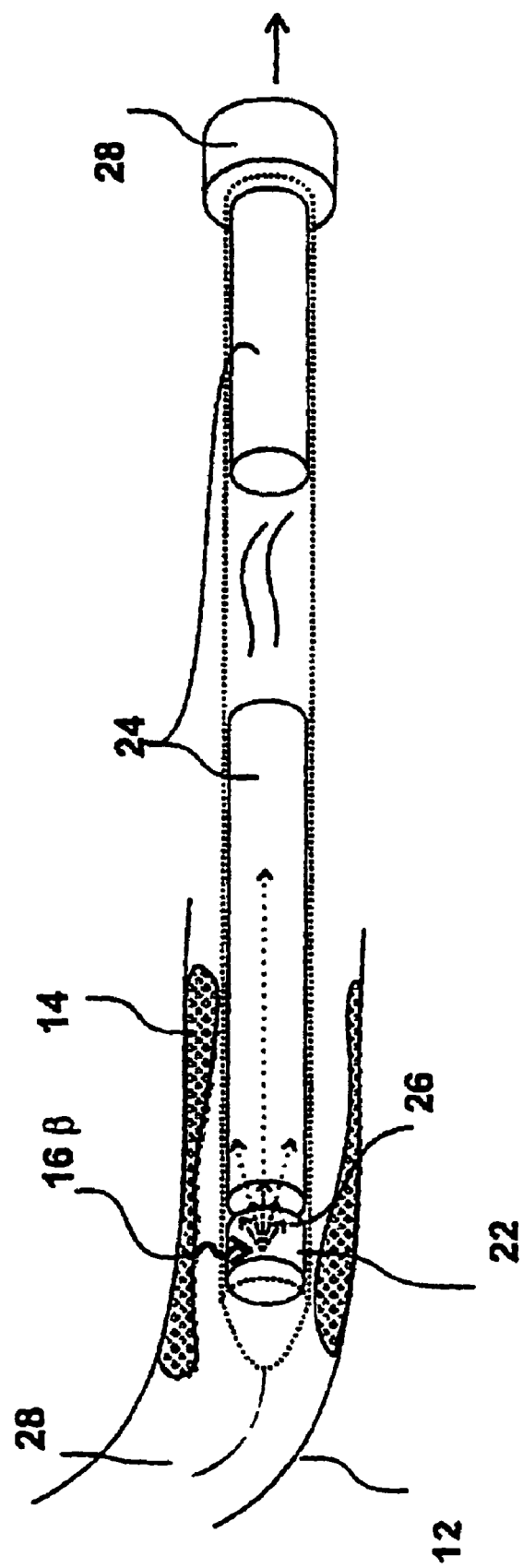
FIG. 2 is a partial cross sectional schematic view of a single-fiber scintillation "camera" employing a scintillating fiber coupled to an optical fiber.

A specific embodiment of the intravascular imaging probe tip 20 constructed in accordance with the principles of the present invention is comprised of a scintillating fiber 22 coupled to a clear optical fiber 24 as shown in FIG. 2. Scintillating fibers 22 are detectors formed by mixing scintillating phosphors (1-2%) with the polystyrene that forms the core of the most popular plastic optical fiber. By having the phosphor in the core, the maximum amount of scintillation light 26 will find its way down the clear optical fiber 24 to the photodetector 28. The scintillation fiber 22 is coupled to a clear optical fiber 24 for the delivery of the light to some distance from the site of the radiation. The simplest form of such a detector for intra-vascular imaging would be a single segment of the scintillating fiber 22 coupled to a single clear fiber 24, which is in turn coupled to a photodetector 28. The device would be inserted through a catheter system 70 and by measuring the count rate as the device is stepped along the artery, the distribution of radioactivity would be "imaged". The key parameters of the device are the stopping power of the scintillating fiber for the electron, the light yields, and the change in light yield if the fiber is bent in the process of being placed in the artery or guided through it.

Scintillating fibers attached to optical fibers and a photomultiplier tube produce strong signals at the photomultiplier in the laboratory. For example, 3-HF scintillating fibers emitting at 535 nanometers irradiated with a 204T1 source, which emits betas at a energy similar to 18F produced strong signals at the PMT. Even if the fiber optic is twisted in a series of decreasing diameter loops the strength of the signal is virtually unchanged down to a 1.5 cm radius of curvature. At 1.0 cm the fiber optic becomes permanently distorted. In order to accommodate tight radii of curvature, bundles of smaller fibers can be used.

Figure 3:
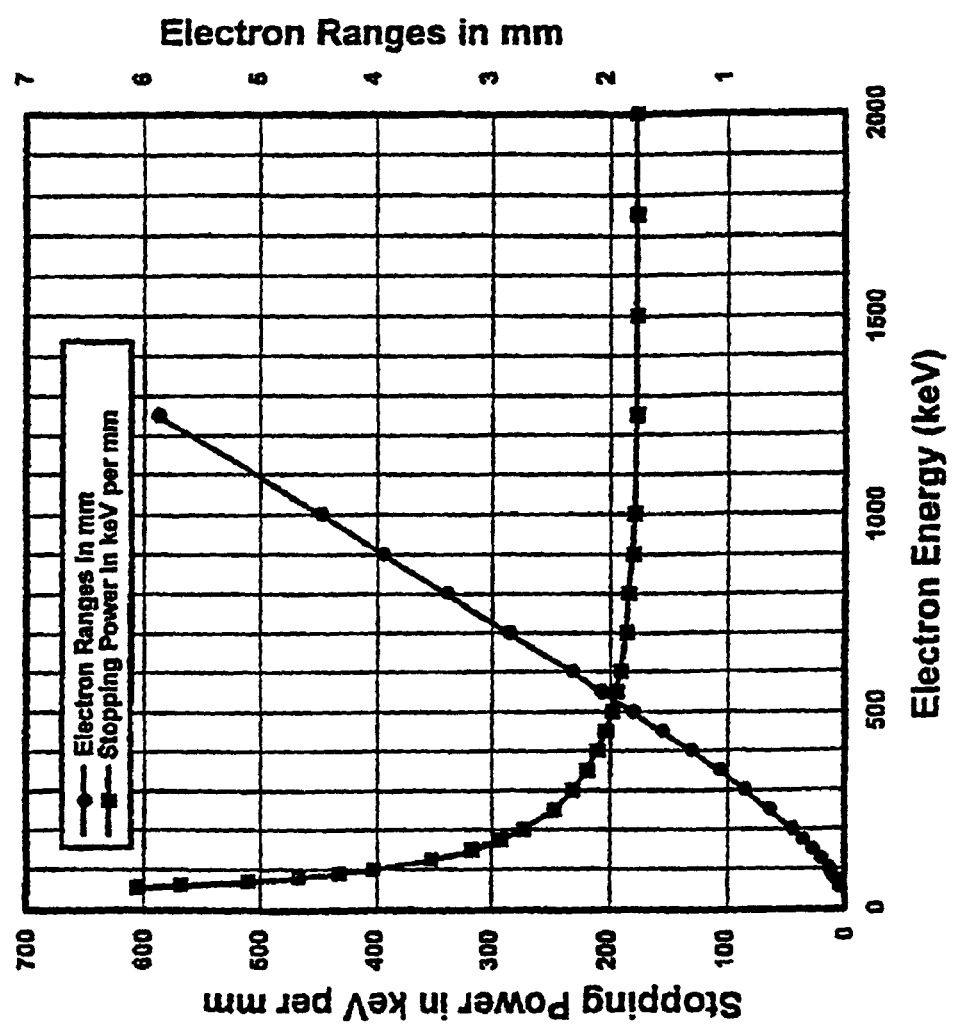
FIG. 3 is a graph showing the calculated stopping power of electrons up to 2 MeV and the range of electrons in polystyrene up to 1250 keV. A 1 mm fiber will stop 300 keV electrons and above 300 the stopping power is close to 200 keV per mm.

The calculated stopping power for electrons up to 2 MeV and the range of electrons in polystyrene up to 1.25 MeV are shown in FIG. 3. From the figure we see that a 1 mm fiber will stop 300 keV electrons and above 300 the stopping power is close to 200 keV per mm.

The amount of light produced varies as a function of maximum electron energy for different beta sources. Light produced by 300 key is adequate for intravascular imaging. A 1 mm or greater diameter fiber is adequate for all likely radioisotopes. The device can be constructed using short segments of scintillating fibers glued to optical fibers. The light can be transmitted down lengths of fiber up to several meters. The light emission is in the range from 400 to 600 nanometers.

Various types of scintillating fibers can be used for the purpose. Since the stopping power is essentially the same for all the fibers, the light yield can be optimized by choice of scintillator, fiber optic, or the like.

Figure 4:
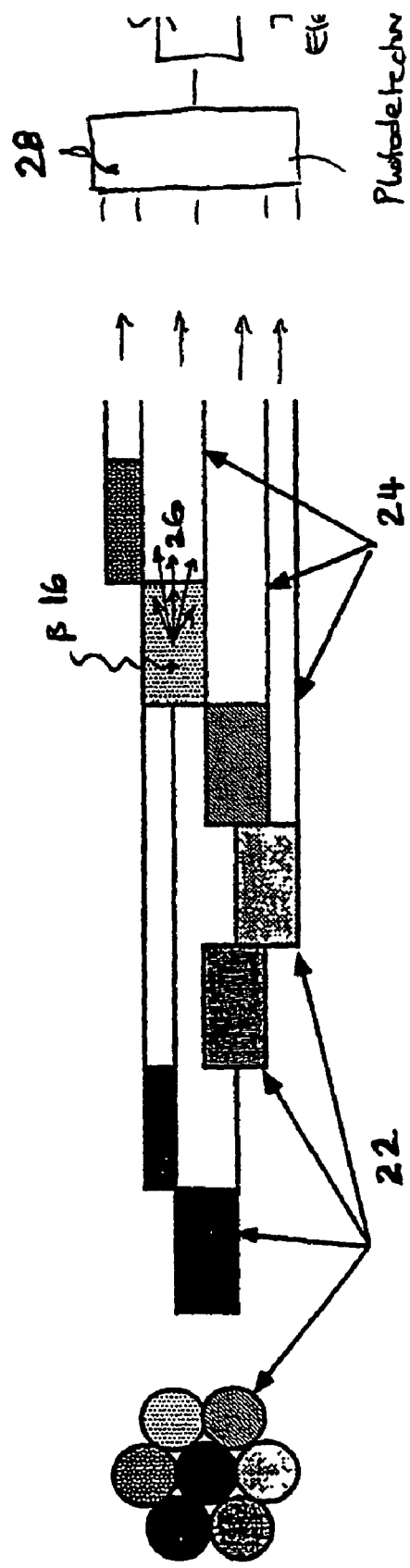
FIG. 4 is a partial cross sectional schematic view of a multi-fiber scintillation "camera" employing a bundle of scintillator fibers each coupled to an optical fiber. Physical offset between the fibers will be used to provide position information.

In one embodiment of an intravascular imaging probe tip 20 constructed in accordance with the principles of the present invention a bundle of scintillating fibers 22 are coupled to clear optical fibers 24 as shown in FIG. 4 wherein the scintillating fibers 22 are offset. The offset provides the position information.

One such embodiment starts with seven 0.3 mm scintillating fibers 22 so that the overall diameter is still ~1 mm. The stopping power of each of the 0.3 mm fibers 22 is high enough to absorb 60 keV, which is adequate for the intravascular imaging system.

The resolution and sensitivity of the multifiber system is controlled by the length of the scintillator segments 22. For instance, 2 mm segments give a very high resolution low sensitivity system that covers only 14 mm, while 7 mm segments give a low resolution high sensitivity system that covers approximately 49 mm. The physical design of this system has some practical implications in that the leading end is narrow and can get into tighter places than the single fiber system. It should be appreciated however, that in other configurations, the arrays of scintillators can be distributed along a length between less than approximately 5 mm to 50 mm, or more.

In one exemplary arrangement, the probe uses scintillation fibers coupled with plastic fibers to a position sensitive photomultiplier tube (PSPMT). The scintillation fibers and clear fibers are 5 mm to 7 mm and 1.5 m in length, respectively, and 0.5 mm in diameter. There are six scintillation fibers, each offset by 6 mm to yield an imaging device which surrounds a guide wire. The detector assembly is 1.9 mm in diameter and 38 mm in length. The fibers are surrounded by a thin, flexible, plastic tube to shield it from outside light. The fibers are connected to the PSPMT with a snap on connector. The PSPMT image is decoded with software to give a linear image. The imaging probe can also run in a mode that has an audio output corresponding to the total level of detected unstable plaque. The device has been tested by stepping a $^{204}$T1 point source past detector to verify function. $^{204}$T1 betas are close in energy to $^{18}$F betas. System resolution is 6 mm when the source is 1 mm from the detector.

Figure 5:
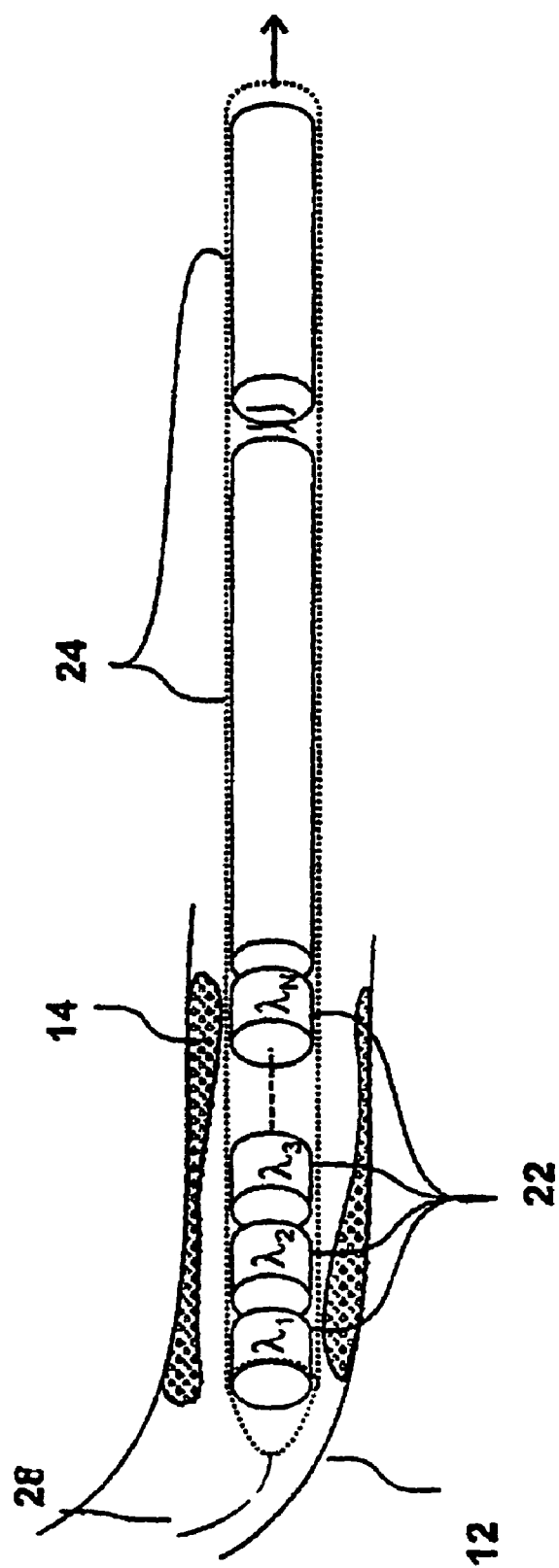
FIG. 5 is fragmentary, exploded perspective view illustrating, in simplified form one embodiment of an apparatus constructed in accordance with the present invention employing a scintillating fiber "camera" employing a number of different scintillators, each with an emission spectrum that is offset in wavelength from the others. The detector is readout by a wavelength dispersing spectrometer.

In one embodiment of an intravascular imaging probe tip 20 constructed in accordance with the principles of the present invention a number a different scintillator fibers 22 are used, each with an emission spectrum that is offset in wavelength from the others as shown in FIG. 5. A suitable detector can be constructed from commercially available scintillating fibers that cover the range from less than 400 nanometers to greater than 600 nanometers. The series of segments 22 are stacked as indicated in FIG. 5 with the longest wavelength segment ($\lambda_1$) at the tip with incrementally shorter wavelengths ($\lambda_2$-$\lambda_n$) as one advanced towards the clear optical fiber 24. The longer wavelength emissions will not have the energy to excite the fluorescent levels in the shorter wavelength scintillators and should be easily transmitted through the downstream segments. The light will be transmitted to spectrometer 29 that uses a grating or other wavelength dispersive medium to spread out the light over a position sensitive photodetector. This creates a spectrum from the light emitted from the scintillating fibers and with calibration there is a one to one correlation between position and wavelength, which is then turned into a linear image of the artery. A suitable 29 is the CHEM2000-UV-VUS Spectrophotometer by Ocean Optics, Inc.

The types of detectors 20 described in the previous three embodiments of the subject invention give a high degree of patient safety in that they require no electrical connections and use no potentially dangerous substances and no high pressures.

Figure 6:
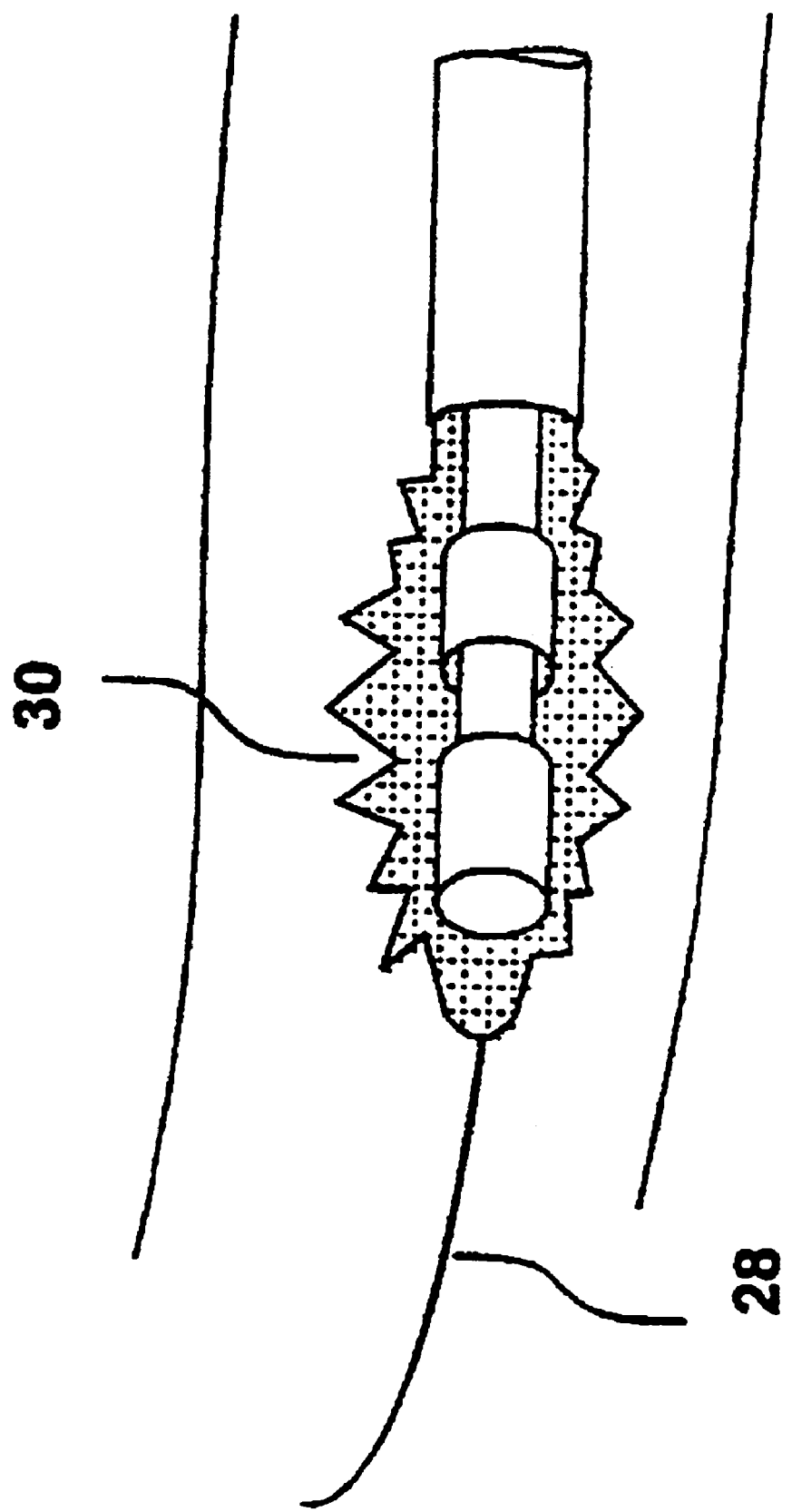
FIG. 6 is a fragmentary, exploded perspective view illustrating, in simplified form one embodiment of an apparatus constructed in accordance with the present invention, employing a liquid primary/fiber secondary scintillation pair detector. In this figure the balloon is deflated during guidance through the artery towards a plaque.
Figure 7:
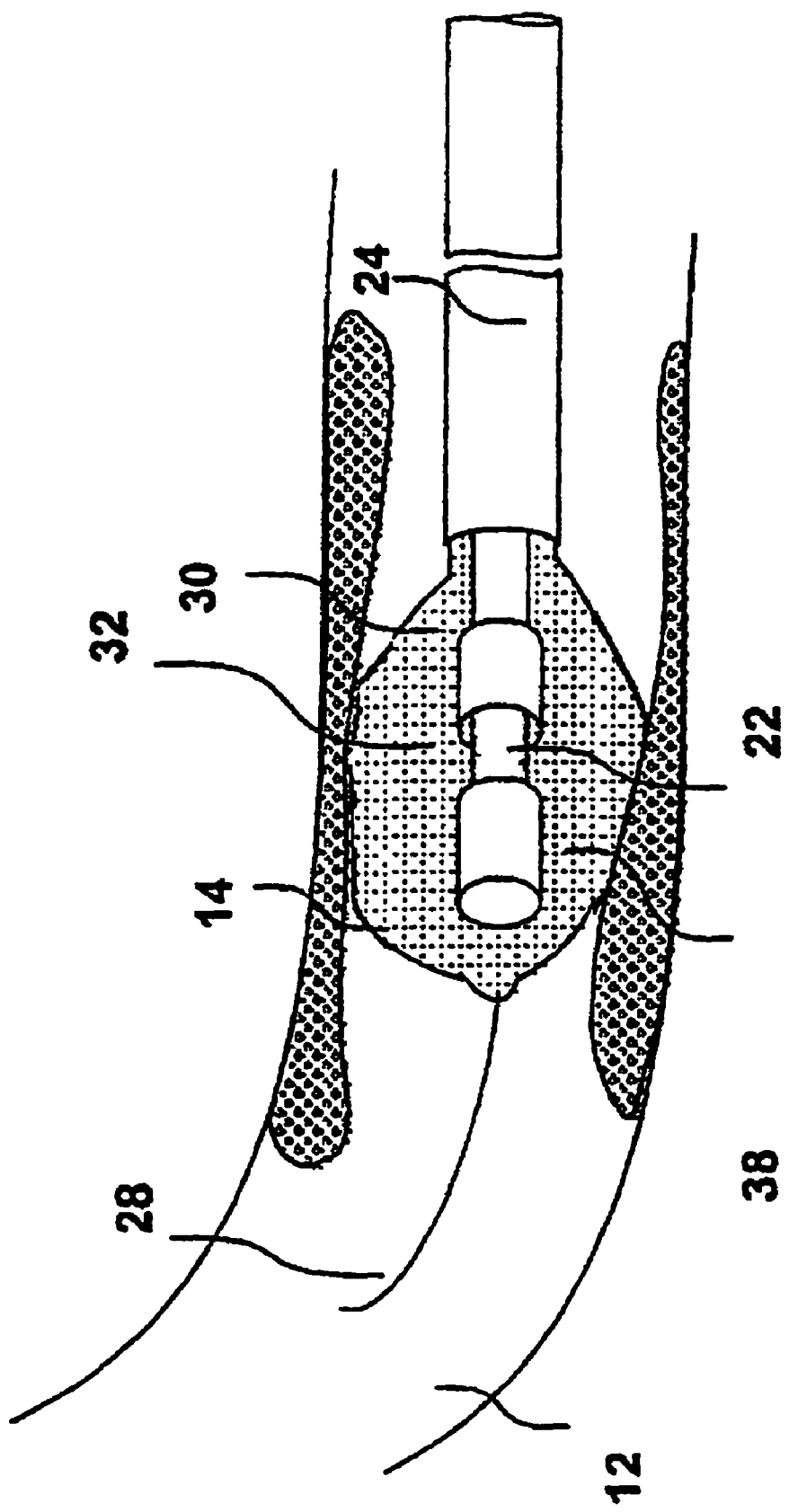
FIG. 7 is a fragmented, exploded perspective view illustrating, in simplified form one embodiment of an apparatus constructed in accordance with the present invention, employing a liquid primary/fiber secondary scintillation pair detector. In this figure the balloon is inflated in the artery at the site of plaque.

In one embodiment of an intravascular imaging probe tip 20 constructed in accordance with the principles of the present invention a balloon 30 is advanced up the artery 12 in a collapsed state as shown in FIG. 6. A 5 cm to 10 cm long scintillating fiber 22 attached to a clear fiber 24, is constructed inside the balloon 30 as shown in FIG. 6 and FIG. 7. When the balloon 30 has reached the region of interest containing a suspect plaque 14, it is inflated with a liquid scintillation solution 32 as shown in FIG. 7. The primary liquid scintillator 32 can provide more mass for stopping power.

Figure 8:
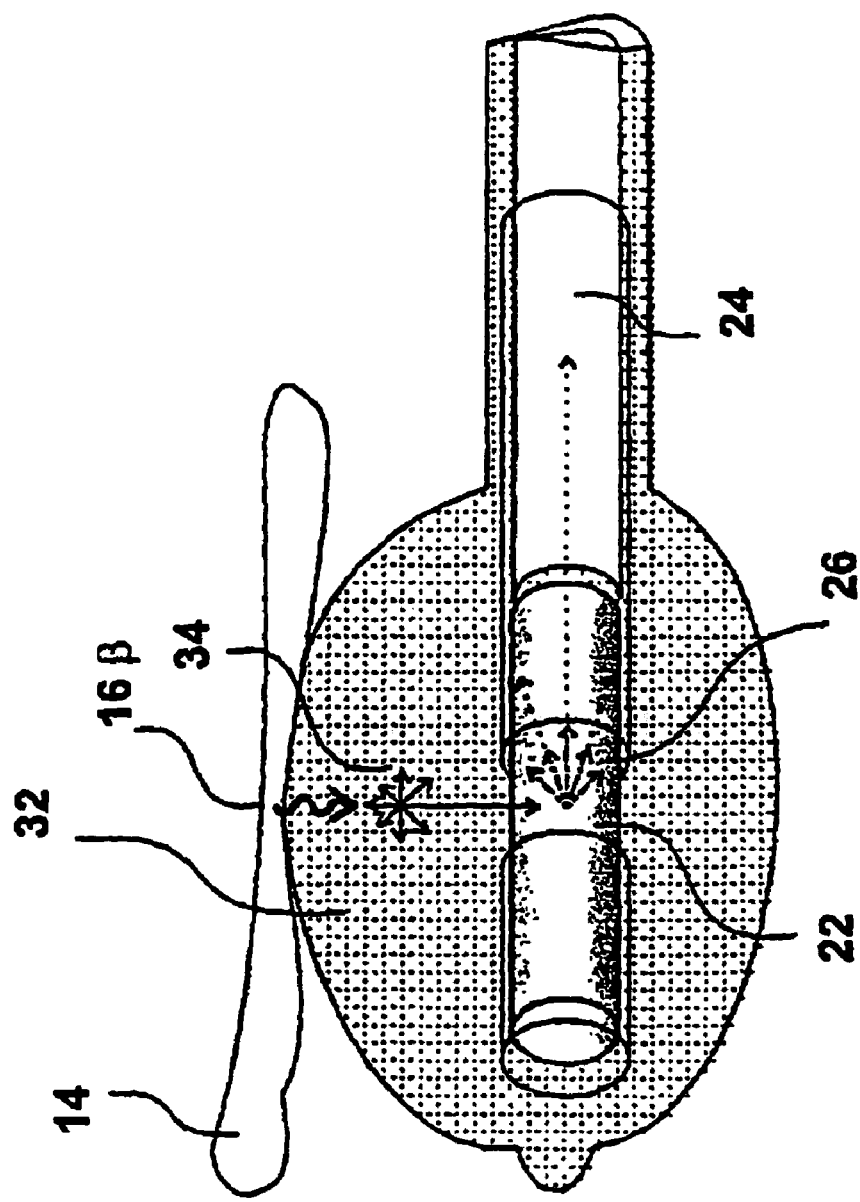
FIG. 8 is a fragmentary, exploded perspective view illustrating the operating principal of the liquid primary scintillator/fiber secondary scintillator pair.

The primary liquid scintillator 32 contains the primary fluor, which absorbs a beta particle 16 and emits short wavelength primary scintillation light 34. The core of the scintillating fiber optic 22 contains a secondary fluor which efficiently absorbs the photons from the primary fluor 34 and them emits longer wavelength light 26 which travels down the clear optical fiber 24 as shown in FIG. 8. A sliding light shield 38 provides position sensitivity as shown in FIG. 7. During gross count mode, the sliding light shield 38 can be moved away from the fiber optic 22 to allow radiation to interact with the entire fiber optic. When in the imaging mode, the sliding light shield 38 can be moved over the fiber optic 22 to provide position sensitivity. The cross section of the inflated balloon gives a factor of 2 to 3 better geometric efficiently for the betas and the extra thickness stops a greater fraction of the higher energy betas compared with the scintillation fiber embodiments described in FIGS. 2-5. The balloon 30 is constructed of a material that is both strong and that will not dissolve in solvents such as toluene, which is typically used in the manufacture of liquid scintillators.

Figure 9:
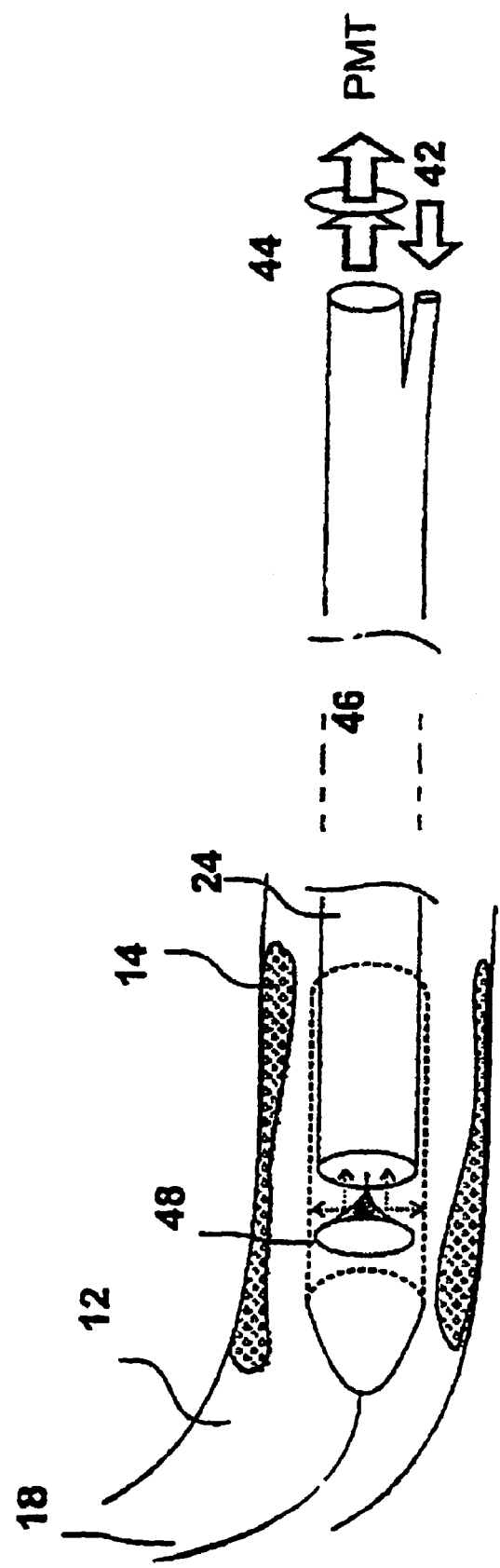
FIG. 9 is a fragmented, exploded perspective view illustrating the operating principles of the imaging storage phosphor detector.
Figure 10:
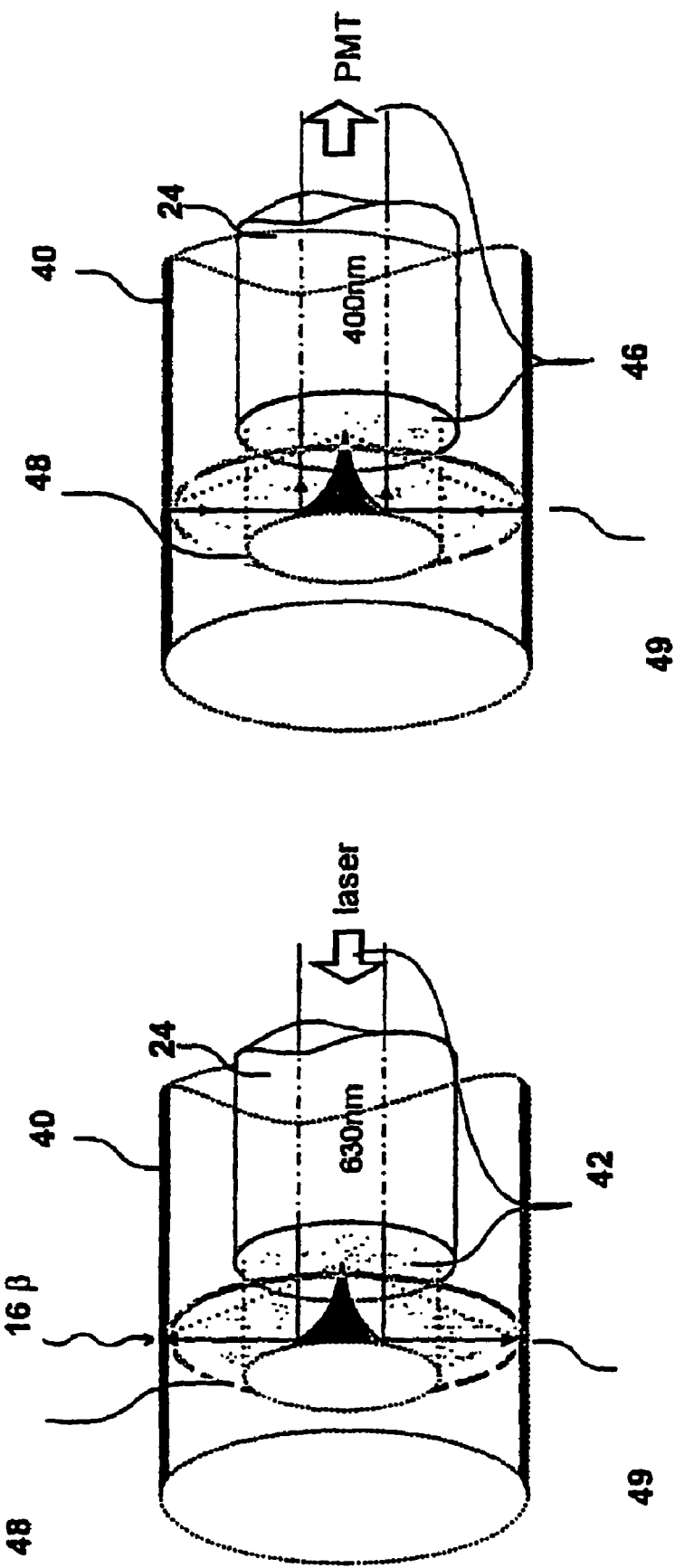
FIG. 10 is a fragmentary, exploded perspective view illustrating the operating principal of the imaging storage phosphor detector wherein a specially shaped mirror at the front of the optical fiber is used to enhance the excitation and reading process from the imaging storage phosphor detector.

In one embodiment of an intravascular imaging probe tip 20 constructed in accordance with the principles of the present invention a scintillating phosphor imaging plate 40 is formed in the shape of a tube ~5 cm long surrounding a clear optical fiber 24 as shown in FIG. 9. The imaging plate 40 is used to read the distribution of betas recorded on the imaging plate. The detector is optimized for stopping beta particles 16, and has mechanical flexibility for movement in the arteries 12. The intravascular imaging probe tip 20 constructed in accordance with the principles of the present invention has the capability of integrating the signal from many beta events in the storage phosphor 40. The stored energy remains stable until scanned with a laser beam 42 through a clear optical fiber 24. The same optical fiber 24 is used for delivery of the laser light 42 and transmission of the read out light 46 corresponding to the stored image as shown in FIGS. 9 and 10. This can be accomplished with use of a filter 44 use to the difference between the wavelength of the laser excitation light 42 (630 nm) and the wavelength of light 46 (400 nm) released upon laser excitation. As can be seen in FIGS. 9 and 10 a concave conical shaped mirror 48 can be used at the front of the clear optical fiber 24 to focus the light to an annulus 49, enhancing the excitation and reading process at the specific desired location. The scanning of the image can be implemented by movement of the optical fiber 24 together with its integrated mirror 48 along the image plate 40.

In one embodiment of an intravascular imaging probe 20 constructed in accordance with the principles of the present invention a silicon (or other semiconductor) based beta detector is used for intravascular imaging. The basic detector concept that we will begin with is a string of individual Si-pin detectors 52 configured in strips 53 as shown in FIG. 11.

Figure 13:
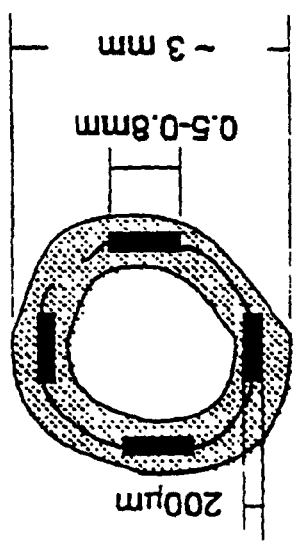
FIG. 13 is a fragmentary, exploded perspective view illustrating the operating principal of the inflated balloon with four strips of silicon detectors arranged in the inflated balloon.

As shown in FIG. 12 the individual detector elements 52 will be connected in series to form flexible linear arrays 50 that can be placed between inner 54 and outer 55 layers of a balloon 30 as shown in FIG. 11. The balloon 30 will be compressed during guidance through the artery 12 to the plaque as shown in FIG. 11. The cardiologist will monitor the summed signal of all detectors 52 during this transit. When the signal suggests high uptake and possible unstable plaque the balloon can be inflated so that the detectors are pressed against the plaque 14 in the artery wall 12 as shown in FIG. 12. In one embodiment of this detector there are between one and four strips 53 fitted into catheters 70 of various French. A scale drawings of one embodiment of an inflated balloon 30 with four strips 53 is shown FIG. 13. In the clinical setting the cardiologist will choose the catheter lumen based on the specific information about the state of the patients arteries.

Figure 14B:
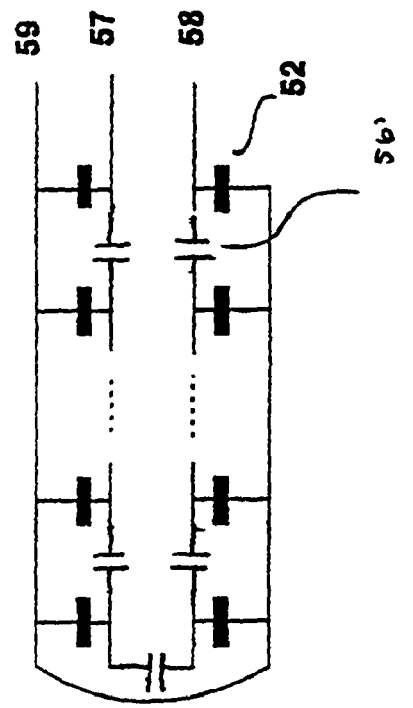
FIG. 14B is a fragmentary, exploded perspective view illustrating the operating principal of the capacitor chain connecting the detectors which will be used to provide signals, the ratio of the signal to a common signal can give the position information.
Figure 14A:
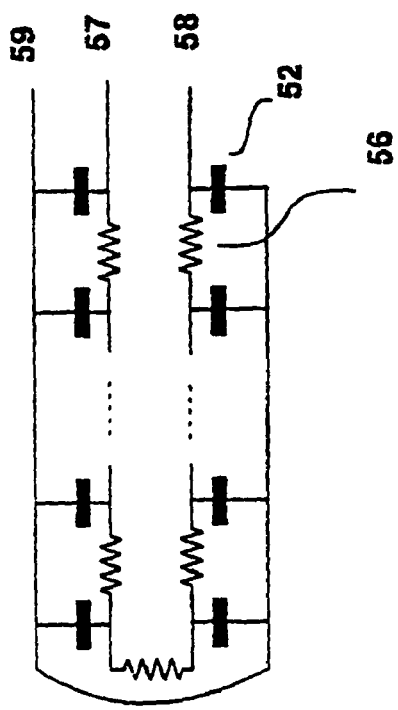
FIG. 14A is a fragmentary, exploded perspective view illustrating the operating principal of the resistive chain connecting the detectors which will be used to provide signals, the ratio of the signal to a common signal can give the position information.

The semiconductor detector based intravascular probe tip 20 can use a chain of resistors 56 (or chain of capacitors 56') connecting the detectors as shown FIGS. 14A and 14B. The detectors and their readout chain (a thick film technology) can be placed on a thin flexible PC board. The signal is read out from either end of the chain (Ladder 1 57 and 2 58). The ratio between a common signal and the signal from the chain provides information about which pixel the beta interaction took place in.

The detectors 52 of the present invention can operate in the photovoltaic mode which allows the detector to operate passively, using the built-in junction potential.

The detectors 52 of the present invention can operate under a bias voltage 59 as shown in FIG. 14. The detectors are fabricated using extremely high resistivity starting material in order to minimize the voltage that needs to be applied to the detector to deplete it. Si-pin detectors fabricated from >10 kohmcm material yield full depletion with just 8 volts of applied bias and <800 pA/cm$^2$ leakage current. The Si starting material is polished to 200 microns or thinner. In this case the dark current can be <5 pA (even at body temperature) for the diodes with 0.5×0.5 mm$^2$ active area.

The detectors 52 of the present invention are fabricated with guard ring structures to reduce the current. This occupies some space at the edge of each device. The 5 0.5×0.5 mm$^2$ active area devices can be implemented on 0.75×0.75 mm$^2$ die.

Figure 15:
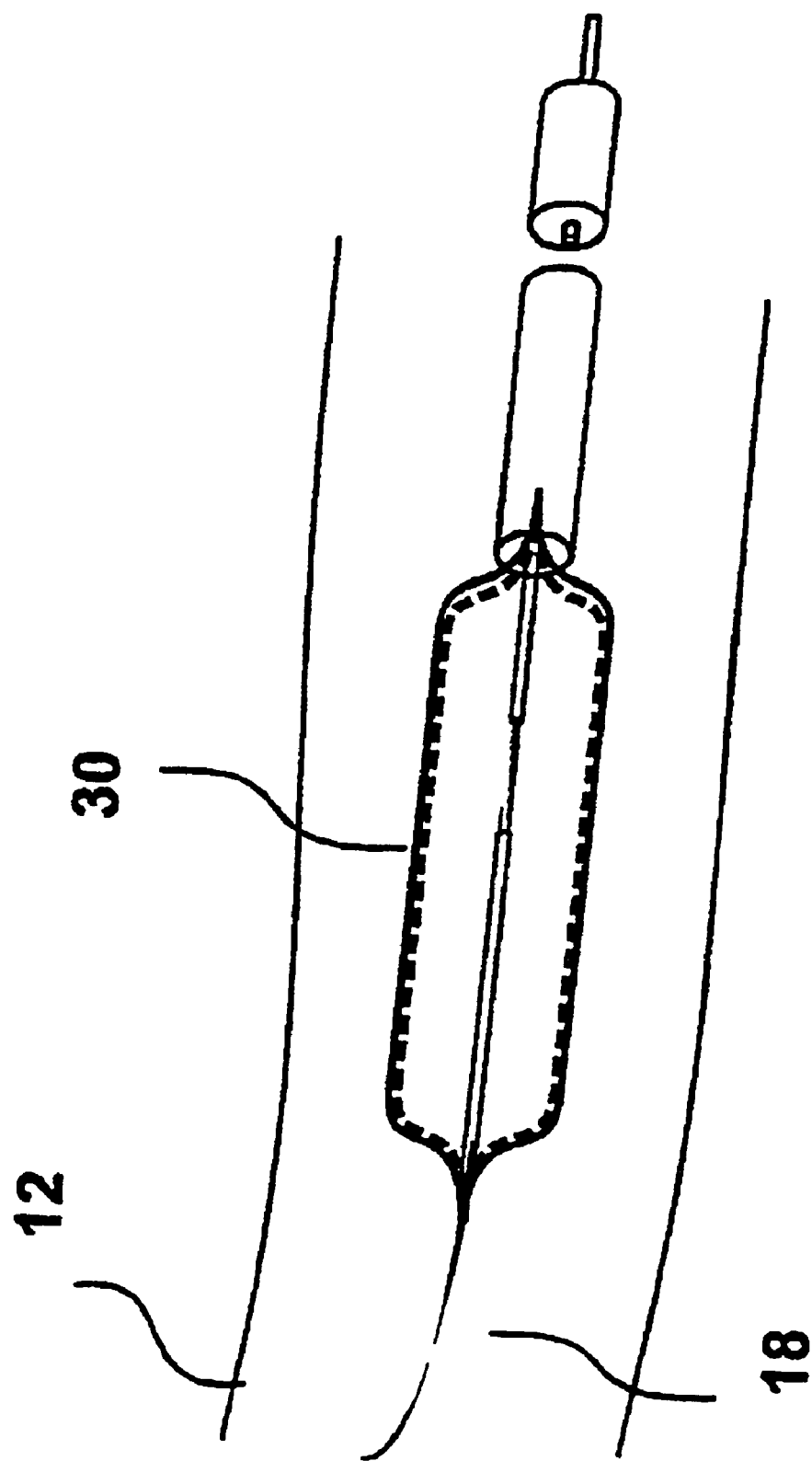
FIG. 15 is a fragmentary, exploded perspective view illustrating the operating principal of the ionization chamber detector showing how the device appears when the balloon is collapsed during advancing up the catheter.
Figure 16:
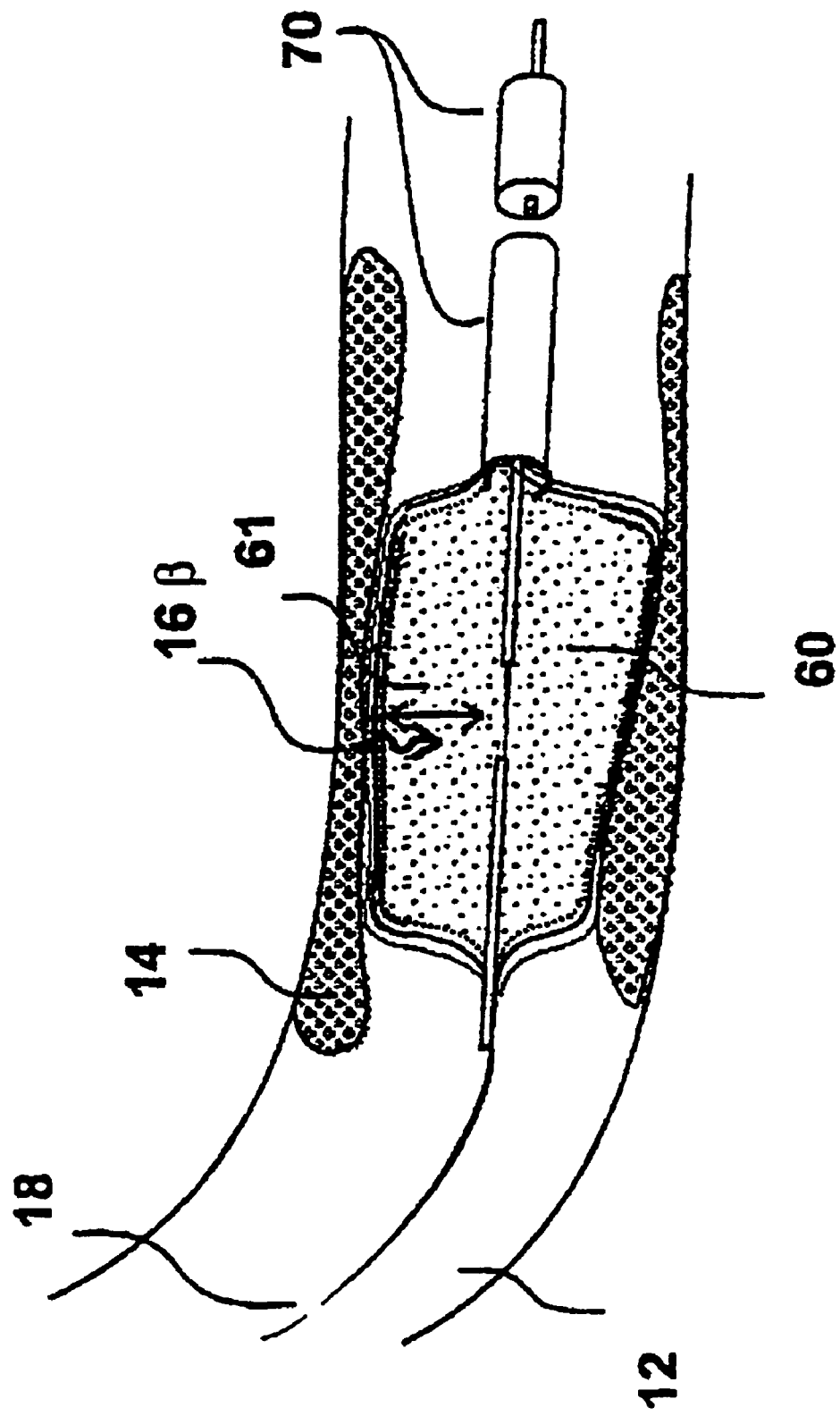
FIG. 16 is a fragmentary, exploded perspective view illustrating the operating principal of the ion chamber detector, showing how, upon reaching the region of interest the balloon is inflated with Xenon gas.
Figure 17:
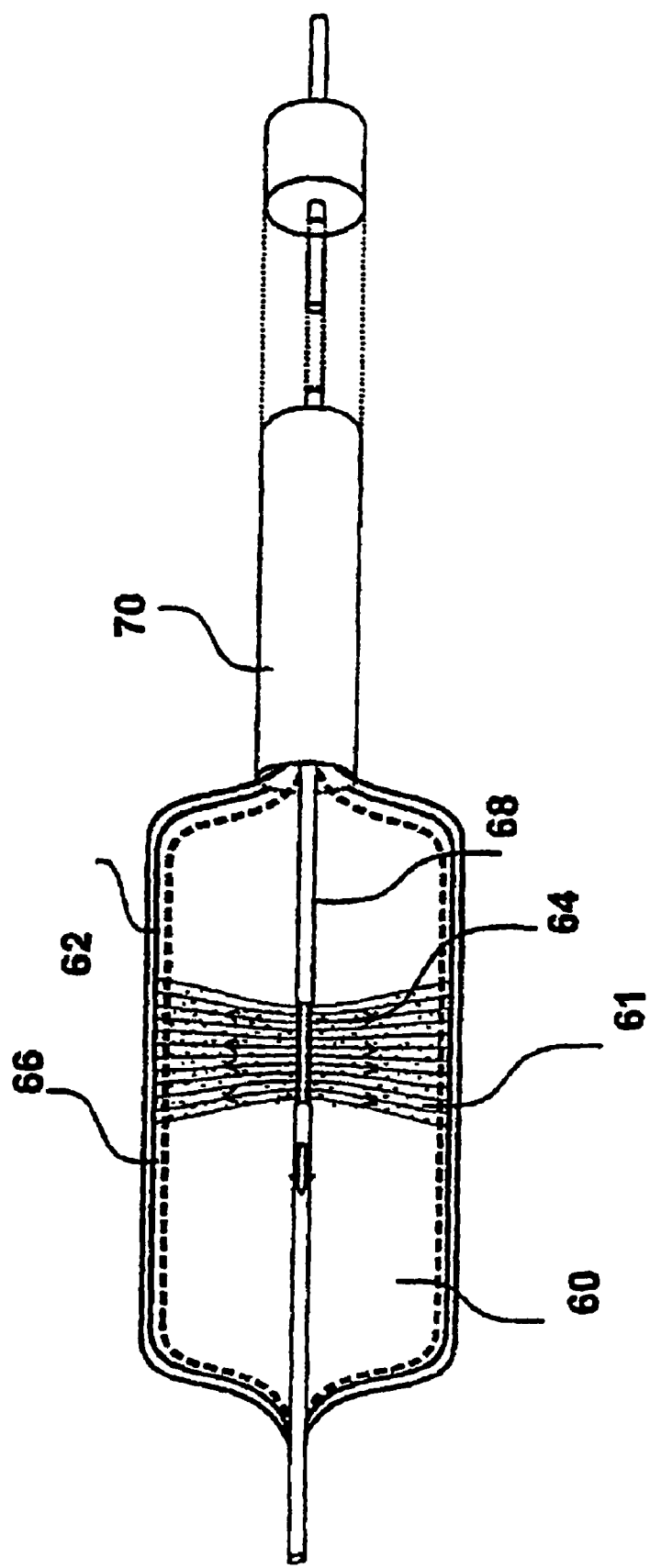
FIG. 17 is a fragmentary, exploded perspective view illustrating the operating principal of the ionization chamber with the cathode formed by embedding a set of parallel wires in the balloon.

In one embodiment an intravascular imaging probe tip 20 is constructed in accordance with the principles of the present invention by filling a balloon 30 with Xenon gas 60 as shown in FIGS. 15 and 16. The detector is then operated as an ionization chamber with the anode formed from a wire 64 running through the center of the balloon 30 and the cathode 62 formed by embedding wires (or wire mesh) in the balloon as shown in FIG. 17. The cathode wires 64, which are at ground potential, can by physically attached to the inside of the balloon and a further insulating mesh 66 can be attached on the inside of the cathode or surrounding the anode. An insulated sleeve 68 can be used to give the system its positioning information. With the sleeve 68 pulled back completely the detector can be operated as a non-imaging highly efficient counter.

Figure 18:
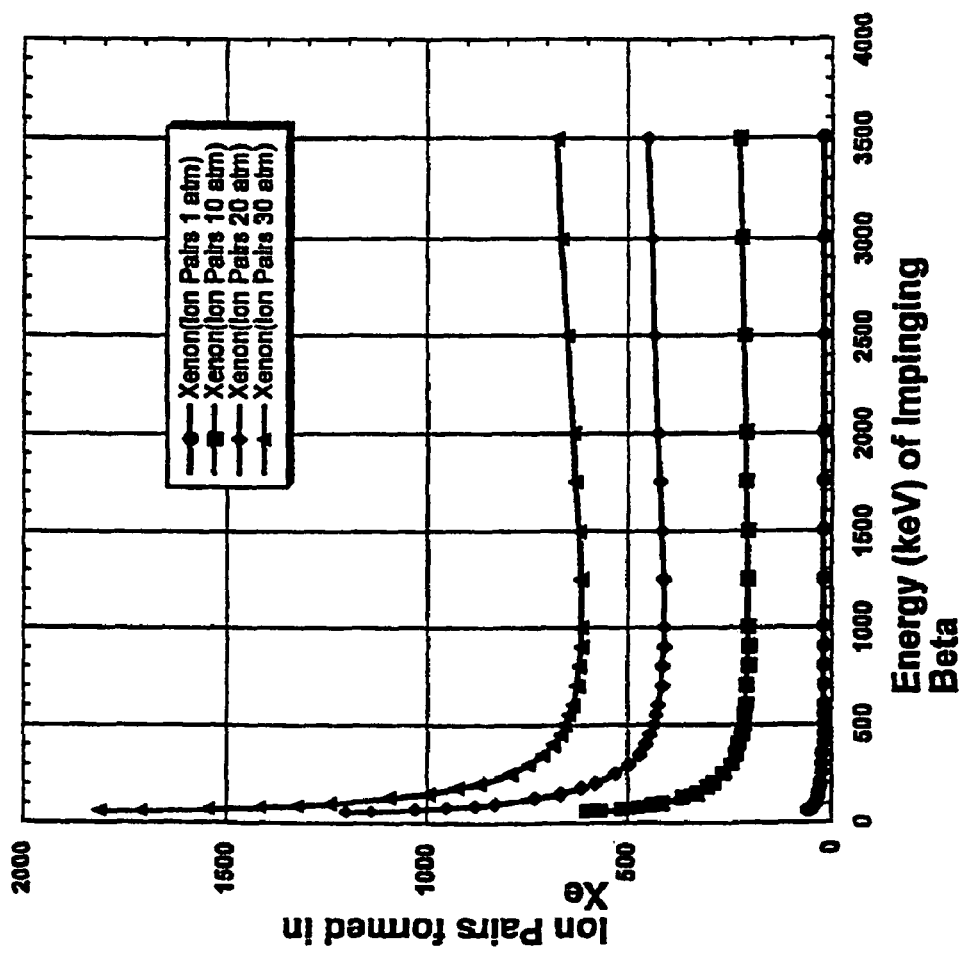
FIG. 18 is a graph showing the calculated ion pairs produced as a function of electron energy at various values of the pressure for a 1 mm detector.

The detector can be operated at 10 and 20 volts on the anode. Protection circuitry can be designed to shutdown the supply voltage instantly when the current approaches a dangerous level such as one nano-amp. In a gas detector constructed in accordance with the principles of the present invention the conversion of deposited energy is much more efficient than the secondary process of scintillation. Thus, although the Xenon gas has low stopping power relative to a solid or liquid the number of ions pairs still significant. FIG. 18 gives the ion pairs produced as a function of electron energy at various values of the pressure for a 1 mm detector. We see that at 10 atm at least 200 ion pairs are produced for all energies. If the balloon is expanded, the number of ion pairs could increase to 600. Low noise preamplifiers with 20-100 electrons rms can handle this number of electrons and provide a good signal to noise ratio. At higher gas pressures there will be a concomitant increase in the signal as shown in FIG. 18. Pressures up to 10 atm or beyond are practical.

In another aspect, the present invention provides kits including catheters, instructions for use and a package. The catheters will generally be those as described above and the instruction for use (IFU) will set forth any of the methods described above. The package may be any conventional medical device packaging, including pouches, trays, boxes, tubes, or the like. The instructions for use will usually be printed on a separate piece of paper, but may also be printed in whole or in part on a portion of the packaging. Optionally, the kits can include a guidewire, radiopharmaceuticals for bonding to the unstable plaque, or the like.

As will be understood by those of skill in the art, the present invention may be embodied in other specific forms without departing from the essential characteristics thereof. For example, while some embodiments of the imaging detectors are shown and described as being disposed on a balloon, other embodiments of the catheters can be manufactured without the balloon. Accordingly, the foregoing description is intended to be illustrative, but not limiting, of the scope of the invention which is set forth in the following claims.

What is claimed is:

1. An intravascular imaging probe comprising:
a body comprising a proximal portion and a distal portion;
an optical fiber movably disposed within the body;
an imaging plate disposed on the distal portion of the body about a distal portion of the optical fiber, wherein beta radiation is absorbed and stored as stable energy in the imaging plate; and a laser to deliver a laser light through the optical fiber to excite the stable energy in the imaging plate so as to release light into the optical fiber.

2. The probe of claim 1 wherein the imaging plate comprises phosphor.

3. The probe of claim 2 comprising a filter that filters the released light transmitted through the optical fiber.

4. The probe of claim 1 further comprising a concave mirror positioned at a distal end of the optical fiber that directs the laser beam and released light between the imaging plate and the optical fiber.

5. The probe of claim 1 wherein the laser light has a wavelength of 630 nanometers.

6. The probe of claim 1 wherein the released light has a wavelength of approximately 400 nanometers.

* * * * *